(12) United States Patent
Chow et al.

(10) Patent No.: US 7,390,829 B2
(45) Date of Patent: Jun. 24, 2008

(54) ALPHA-2 ADRENERGIC AGONISTS

(75) Inventors: Ken Chow, Newport Coast, CA (US); Todd M. Heidelbaugh, Fountain Valley, CA (US); Phong X. Nguyen, Placentia, CA (US)

(73) Assignee: Allergan, Inc., Irvine, CA (US)

( * ) Notice: Subject to any disclaimer, the term of this patent is extended or adjusted under 35 U.S.C. 154(b) by 518 days.

(21) Appl. No.: 11/172,229

(22) Filed: Jun. 29, 2005

(65) Prior Publication Data

US 2007/0004789 A1 Jan. 4, 2007

(51) Int. Cl.
*A61K 31/4164* (2006.01)
*C07D 233/04* (2006.01)

(52) U.S. Cl. .................. 514/392; 548/300.1; 548/316.4; 548/323.5; 548/324.5; 514/385; 514/386

(58) Field of Classification Search ............. 548/300.1, 548/316.4, 323.5, 324.5; 514/385, 386, 392
See application file for complete search history.

(56) References Cited

U.S. PATENT DOCUMENTS 6,313,172 B1 11/2001 Chow et al.
2004/0220402 A1 11/2004 Chow et al.

FOREIGN PATENT DOCUMENTS

GB 1 499 485 2/1978

| WO | WO 92/00073 | 1/1992 |
|----|-------------|--------|
| WO | WO 99/28300 | 6/1999 |
| WO | WO 01/00586 | 1/2001 |
| WO | WO2005/039567 | 5/2005 |

OTHER PUBLICATIONS

Otejnik et al (2005): STN International HCAPLUS database, Columbus (OH), accession No. 2005:395087.*
U.S. Appl. No. 10/153,328, filed May 21, 2002, Chow et al.
U.S. Appl. No. 10/891,740, filed Jul. 15, 2004, Gil et al.
Ruffolo, Jr., "α-Adrenoreceptors: Molecular Biology, Biochemistry and Pharmacology", 1991.

* cited by examiner

*Primary Examiner*—Golam M Shameem
(74) *Attorney, Agent, or Firm*—Allergan, Inc.; Martin Voet; Brent A. Johnson (57) ABSTRACT

A compound is disclosed herein comprising

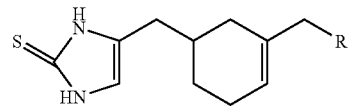

or a pharmaceutically acceptable salt or a prodrug thereof; wherein R is OH or $NH_2$.

Methods, compositions, and medicaments related thereto are also disclosed.

8 Claims, 4 Drawing Sheets

Fig. 1

Oral Dosing of Compound 3 Alleviates Tactile Hypersensitivity

Fig. 2
Compound 1 and its Ester, Compound 3,
Lower Rabbit IOP

Fig. 3
Compound 1 Does Not Sedate Rats

Fig. 4
Oral Compound 3 Has > 300-Fold Therapeutic Window

ALPHA-2 ADRENERGIC AGONISTS

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\alpha_1$, and $\alpha_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a further general background on the $\alpha$-adrenergic receptors, the reader's attention is directed to Robert R. Ruffolo, Jr., $\alpha$-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting $\alpha$-adrenergic receptor affinity is explored.

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha-2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

British Patent 1 499 485, published Feb. 1, 1978 describes certain thiocarbamide derivatives; some of these are said to be useful in the treatment of conditions such as hypertension, depression or pain.

PCT Publications WO01/00586 published on Jan. 4, 2002 and WO99/28300 published on Jun. 10, 1999 describe certain imidazole derivatives acting as agonists of alpha$_{2B}$ and/or alpha$_{2C}$ adrenergic receptors. U.S. Pat. No. 6,313,172 discloses phenylmethyl-thiourea derivatives used for treatment of pain.

U.S. patent application Ser. No. 10/153,328, filed Jun. 19, 2002, teaches an $\alpha$-2 adrenergic agonist having the following structure U.S. patent application Ser. No. 10/891,740, filed on Jul. 15, 2004, teaches an $\alpha$-2 adrenergic agonist having the following structure.

DESCRIPTION OF THE INVENTION

A compound is disclosed herein comprising or a pharmaceutically acceptable salt or a prodrug thereof; wherein R is OH or NH$_2$.

Another compound consists of or a pharmaceutically acceptable salt or a prodrug thereof.

Another compound consists of or a pharmaceutically acceptable salt or a prodrug thereof.

Tautomers of the imidazoles-2-thione moiety are possible for the compounds disclosed herein are possible. Examples of the tautomers are shown below.

For any structure disclosed herein, the scope of a compound also includes any tautomer which may be formed.

One embodiment is a compound consisting of 4-(3-Hydroxymethyl-cyclohex-3-enylmethyl)-1,3-dihydro-imidazole-2-thione or a pharmaceutically acceptable salt or a prodrug thereof.

Another embodiment is a compound consisting of 4-(3-Aminomethyl-cyclohex-3-enylmethyl)-1,3-dihydro-imidazole-2-thione or a pharmaceutically acceptable salt or a prodrug thereof.

The compounds disclosed herein are agonists of $\alpha_2$ adrenergic receptors. Generally speaking α2 agonists, can alleviate sympathetically-sensitized conditions that are typically associated with periods of stress. These include 1) the increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha2 agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

While not intending to limit the scope of the reaction in any way, we have surprisingly discovered that the disclosed alpha2-adrenergic agonists are active without sedation and other characteristic side effects. The compounds exhibit activity in a mouse model of tactile hypersensitivity in which alpha2-adrenergic agonists such as brimonidine (UK14,304) and clonidine are active. The model is dependent on sympathetic nervous system (SNS) activity and may in part reflect sympatholytic actions of alpha2-adrenergic agonists. The disclosed compounds also lower intraocular pressure. The compounds disclosed can be used as analgesics, particularly in chronic pain and visceral pain, with minimal undesirable side effects, such as sedation and cardiovascular depression, commonly seen with other agonists of the $\alpha_2$ receptors.

Other diseases that may be treated with the compounds disclosed herein include, but are not limited to neurodegenerative aspects of the following conditions:

MACULOPATHIES/RETINAL DEGENERATION Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration, UVEITIS/RETINITIS/CHOROIDITIS/OTHER INFLAMMATORY DISEASES Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy VASUCLAR DISEASES/EXUDATIVE DISEASES Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease TRAUMATIC/SURGICAL/ENVIRONMENTAL Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy PROLIFERATIVE DISORDERS Proliferative Vitreal Retinopathy and Epiretinal Membranes INFECTIOUS DISORDERS Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis GENETIC DISORDERS Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum RETINAL TEARS/HOLES Retinal Detachment, Macular Hole, Giant Retinal Tear TUMORS Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

The compounds disclosed herein may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention; conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1-6 carbon atoms, etc: Two examples of useful prodrugs are shown below.

Compound 2

Compound 3

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms, are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer, system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydrokypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Method A

Procedure for the preparation of 4-(3-Hydroxymethyl-cyclohex-3-enylmethyl)-1,3-dihydro-imidazole-2-thione (Compound 1)

Compound 1

8-(2-Benzyloxy-ethyl)-1,4-dioxa-spiro[4.5]decane (Intermediate A1) (1.02 g, 3.70 mmol) (obtained as described in: Ciufolini et. al. J. Amer. Chem. Soc. 1991, 113, 8016, incorporated herein by reference) was dissolved in acetone (100 mL):H$_2$O (5 mL) and reacted with TsOH (140 mg, 0.74 mmol) at 45° C. for 5 h. After a standard aqueous work-up the material was purified by chromatography on SiO$_2$ to give 4-(2-benzyloxy-ethyl)-cyclohexanone as a colorless oil (97%).

A solution of LDA (33 ml, 1.5 M in Et$_2$O) (available from Aldrich) in THF (50 mL) at −78° C. was treated with 4-(2-benzyloxy-ethyl)-cyclohexanone (9.5 g, 40.2 mmol). The mixture was warmed to 0° C. over 30 m before re-cooling to −78° C. and adding HMPA (7 mL). Methyl cyanoformate (4.1 mL, 85 mmol) (available from Aldrich) was added and the mixture was stirred for 15 m before aqueous quench and work-up. The product was purified by chromatography on SiO$_2$ with 10% EtOAc:Hx. 5-(2-Benzyloxy-ethyl)-2-oxo-cyclohexanecarboxylic acid methyl ester was isolated, 5.8 g (49%) and reduced with an equivalent of NaBH$_4$ in MeOH at −10° C. The alcohol (Intermediate A2) was purified by chromatography on SiO$_2$ with 30 to 50% EtOAC:Hx. (~90% yield).

A solution of 5-(2-benzyloxy-ethyl)-2-hydroxy-cyclohexanecarboxylic acid methyl ester (Intermediate A2) (0.72 g, 2.48 mmol) in pyridine (10 mL) was treated with SOCl$_2$ (0.73 mL, 12.4 mmol) (available from Aldrich) at −20° C. The mixture was allowed to react for 15 m and was then warmed to 55° C. for 16 h. The solvents were removed under vacuum and the residue was diluted in ether at 0° C. The solution was quenched with water, washed with 1M, HCl, 5% NaOH and brine. The organic material was dried over MgSO$_4$ filtered and freed of solvent. The mixture was diluted with benzene and water was removed by azeotropic distillation under vacuum. The residue was dissolved in benzene (15 mL) and DBU (0.76 mL, 5 mmol) was added. The mixture was reacted for 30 m at rt. After work-up and chromatography on SiO$_2$ with 20% EtOAc:Hx, 5-(2-benzyloxy-ethyl)-cyclohex-1-enecarboxylic acid methyl ester (Intermediate A3) was isolated 0.56 g (82%).

Intermediate A3 (6.5 g) was dissolved in THF (100 mL) and added to a solution of DIBAL (70 mL, 1M in hexanes) (available from Aldrich) in THF (160 mL) at −35° C. for 35 m. The mixture was quenched with Rochelle's salt solution, and extracted with ether. The dried residue was purified by chromatography on SiO$_2$ with 30% EtOAc:Hx to yield [5-(2-benzyloxy-ethyl)-cyclohex-1-enyl]-methanol 4.6 g (80%). A solution of the alcohol (4.0 g, 18.7 mmol) in DMF (60 mL) was treated with triethylamine (3 mL) followed by TBSCl (3.0 g, 22.4 mol) for 20 m at rt. The residue was isolated from an aqueous work-up and purified by chromatography to give [5-(2-benzyloxy-ethyl)-cyclohex-1-enylmethoxy]-tert-butyl-dimethyl-silane (Intermediate A4) 3.6 g (63%).

The benzyl protected alcohol (Intermediate A4) (2.0 g, 5.55 mmol) in THF (20 mL) was cooled to −70° C. and NH$_3$ was condensed in this flask (~20 mL). Na chunks were added and the mixture was allowed to stir at −70° C. for 15 m. The mixture was warmed to −30° C. for 20 m. The mixture was quenched with NH$_4$Cl and the product was isolated by extraction. The residue was purified by chromatography on SiO$_2$ with 25% EtOAc:Hx (99%). The alcohol was oxidized by the standard "Swern-type" protocol. A solution of oxalyl chloride (33 mL, 2M in CH$_2$Cl$_2$) (available from Aldrich) in CH$_2$Cl$_2$ was cooled to −78° C. DMSO (5.4 mL, 76 mmol) in CH$_2$Cl$_2$ (80 mL) was added via addition funnel over 45 m, and the mixture stirred for an addition 45 m. A solution of the alcohol, 2-[3-(tert-butyl-dimethyl-silanyloxymethyl)-cyclohex-3-enyl]-ethanol (13.7 g, 50.8 mmol) in CH$_2$Cl$_2$ (45 mL) was added over 30 m to this solution at −78° C. After 1 h, NEt$_3$ (14.5 mL) in CH$_2$Cl$_2$ (10 mL) was added over 15 m and the mixture was warmed to rt for 3 h. After standard aqueous work-up and flash chromatographic purification, [3-(tert-butyl-dimethyl-silanyloxymethyl)-cyclohex-3-enyl]-acetaldehyde (Intermediate A5) was isolated 10 g (~75%).

The aldehyde (Intermediate A5) (10 g, 37.2 mmol) in anhydrous ethanol (70 mL) was treated with tosylmethyl isocyanide (7.2 g, 3.7 mmol) (available from Aldrich) followed by addition of a catalytic amount of NaCN (150 mg) at rt for 15 m. The mixture was reduced in volume to about 20 mL under reduced pressure. The residue was dissolved in NH$_3$ (7M in MeOH) and placed into re-sealable tubes and heated to 100° C. for 18 h. The mixture was cooled and the solvent removed under vacuum. The residue was purified by flash chromatography on silica gel with 5% MeOH:EtOAc to remove TsOH and the product was eluted with 5% NH$_3$-MeOH in CH$_2$Cl$_2$ to yield 7 g (60%) of 4-[3-(tert-butyl-dimethyl-silanyloxymethyl)-cyclohex-3-enylmethyl]-1H-imidazole (Intermediate A6).

A mixture of 4-[3-(tert-butyl-dimethyl-silanyloxymethyl)-cyclohex-3-enylmethyl]-1H-imidazole (Intermediate A6) (6.0 g, 19.6 mmol) in THF (100 mL) and water (80 mL) was treated with NaHCO$_3$ (16.8 g) and phenylchlorothionoformate (6.63 mL, 49 mmol) (available from Aldrich). The mixture was stirred for 5.5 h at rt. The mixture was diluted with water (40 mL) and ether (50 mL). The organic layer was removed and the aqueous layer was extracted with ether (2×30 mL). The organic layers were dried over MgSO$_4$ and filtered. The residue was concentrated under vacuum, diluted with MeOH (100 mL) and reacted with NEt$_3$ (15 mL) at rt for 15 h. The solvent was removed under vacuum and replaced with 30% CH$_2$Cl$_2$:hexane. The solvent was removed again and solids formed. The solid was again suspended in 30% CH$_2$Cl$_2$:hexane and collected on a filter. The material was purified by chromatography on silica gel with 3 to 5% NH$_3$-MeOH in CH$_2$Cl$_2$ to give 4-[3-(tert-butyldimethyl-silanyloxymethyl)-cyclohex-3-enylmethyl]-1,3-dihydro-imidazole-2-thione 4.1 g (62%).

A solution of the 4-[3-(tert-butyl-dimethyl-silanyloxymethyl)-cyclohex-3-enylmethyl]-1,3-dihydro-imidazole-2-thione (3 g) in CH$_2$Cl$_2$ (50 mL) and acetonitrile (50 mL) at −10° C. was treated with HF-pyridine (1.9 mL) (available from Aldrich), the ice-bath was removed and the mixture was stirred for no more than 45 m at rt. Solid NaHCO$_3$ was carefully added to the suspension and stirring was continued for 30 m. The solvent was removed under vacuum and replaced with 7% NH$_3$-MeOH in CH$_2$Cl$_2$ and concentrated onto silica gel. The residue was purified by chromatography by elution with 5% NH$_3$-MeOH:CH$_2$Cl$_2$ to 7% NH$_3$-MeOH:CH$_2$Cl$_2$ to yield pure alcohol 4-(3-hydroxymethyl-cyclohex-3-enylmethyl)-1,3-dihydro-imidazole-2-thione (Compound 1) 1.6 g (80%).

$^1$H NMR (300 MHz, MeOD-d$^4$) δ 6.57 (s, 1H), 5.64 (brs, 1H), 3.88 (s, 2H), 3.30 (t, J=1.5 Hz, 1H), 2.45 (d, J=6.9 Hz, 2H), 2.10-2.04 (m, 3H), 1.94-1.70 (series of m, 3H), 1.28-1.15 (m, 1H).

EXAMPLE B

Method B

Procedure for the preparation of Benzoic acid 5-(2-thioxo-2,3-dihydro-1H-imidazol-4-ylmethyl)-cyclohex-1-enylmethyl ester (Compound 2)

A mixture of 4-(3-hydroxymethyl-cyclohex-3-enylmethyl)-1,3-dihydro-imidazol-2-one (Compound 2) (200 mg, 0.9 mmol) in DMF (1.6 mL) and CH$_2$Cl$_2$ (5 mL) was treated with EDCI (256 mg, 1.34 mmol) (available from Aldrich), benzoic acid (144 mg, 1.18 mmol) (available from Aldrich) and DMAP (32 mg, 0.26 mmol) (available from Aldrich). The mixture was stirred for 24 h at rt. The reaction mixture was diluted with EtOAc (30 mL) and washed with water (1×20 mL), 5% HCl (2×20 mL), brine (1×20 mL). The organic layer was separated and dried over MgSO$_4$. The material was freed of solvent and purified by chromatography on SiO$_2$ with 30% to 50% to 70% EtOAc:hexane to give benzoic acid 5-(2-thioxo-2,3-dihydro-1H-imidazol-4-ylmethyl)-cyclohex-1-enylmethyl ester (Compound 2) as a foamy solid, 155 mg (53%).

$^1$H NMR (300 MHz, CDCl$_3$) δ 11.0 (s, 1H), 10.4 (s, 1H), 8.05-8.02 (m, 2H), 7.58-7.42 (m, 3H), 6.43 (s, 1H), 5.81 (s, 1H), 4.66 (s, 2H), 2.56-2.40 (m, 2H), 2.18-1.74 (m, 5H), 1.31-1.24 (m, 2H).

EXAMPLE B-1

Use of cyclopentyl acetic acid (commercially available from Aldrich) in Method B produced cyclopentyl-acetic acid 5-(2-thioxo-2,3-dihydro-1H-imidazol-4-ylmethyl)-cyclohex-1-enylmethyl ester (Compound 3) (38%).

$^1$H NMR (300 MHz, CDCl$_3$) δ 11.4 (brs, 1H), 11.2 (brs, 1H), 6.49 (s, 1H), 5.72 (s, 1H), 4.42 (s, 2H), 2.51-2.48 (m, 2H), 2.35 (d, J=7.5 Hz, 2H), 2.25-2.05 (m, 1H), 1.84-1.16 (series of m, 15H).

Procedure for the preparation of 4-(3-aminomethyl-cyclohex-3-enylmethyl)-1,3-dihydro-imidazole-2-thione (Compound 4)

In a 72-L, four-necked, round-bottomed flask equipped with a mechanical stirrer, a Teflon coated thermo-couple, an addition funnel, and a nitrogen inlet were placed, under nitrogen, Zinc dust, (<10 micron particle size, was purchased from SIGMA-ALDRICH, Inc) (1985 g, 30.5 mol) and dry tetrahydrofuran (19.5 L). The mixture was cooled to 0° C. using an efficient cooling bath and dibromomethane (2110 g, 12.1 mol) was added dropwise over 15 min maintaining the temperature at 0° C. After stirring for 15 min at 0° C., the reaction mixture was cooled to −40° C. Titanium (IV) chloride (2303 g, 12.1 mol) was added dropwise over 1½ h at −40° C. Caution: The addition of $TiCl_4$ is very exothermic. The cooling bath was held at −60° C., and the reaction temperature was held at −45 to −35° C., during this charge. If the $TiCl_4$ charge is done too rapidly, the reaction mixture tends to solidify to a solid mass. The resulting reaction mixture was allowed to warm to 0° C. (~2-3 h) and then stirred at that temperature for an additional 3 h. Intermediate C1 (obtained according to procedures in Webster, F. X. et. al. *Synthesis* 922, 1987) (425 g, 3.03 mol) was added as a solid, in 50-100 g portions over 30 min maintaining the temperature 0-10° C., using a cooling bath held at −20° C. The resulting greenish-brown reaction mixture was allowed to stir overnight while warming to ambient temperature. After the reaction was complete as judged by HPLC (Note), the batch was cooled to 0° C. and carefully quenched with 1M $NaHSO_4$ (31.9 L, 31.9 mol) keeping the temperature at 0-10° C. (1-1.5 h). The pH of the dark black aqueous mixture was typically 2-3. After the $NaHSO_4$ addition was complete, the resulting mixture was extracted with hexanes (2×7 L). The organic extracts were combined and extracted with 1N NaOH (1×12 L and 2×6.6 L). The aqueous NaOH layers were combined, transferred back into the reaction flask along with hexanes (7 L), cooled to 15° C. and acidified with 33% aqueous $NaHSO_4$ (9 L) to pH 1-2 while maintaining the temperature between 15-25° C. The mixture was stirred vigorously for 1-2 minutes, and then the layers were separated. The batch was extracted a second time with hexanes (7 L). The combined organic portions were dried ($MgSO_4$, 200 gm) and concentrated in vacuo at 30-35° C. to yield 290 g of Intermediate C2 as a clear pale-yellow oil containing ~15-17% hexanes (57% yield).

To a three neck flask equipped with an addition funnel, thermocouple and a $N_2$ inlet, was added a THF (anhy., 200 mL) solution of the carboxylic acid, Intermediate C2 (40 g, 0.290 mol). This solution was cooled to 0° C. The addition funnel was charged with tetrabutylammonium hydroxide (TBAH, 40% in $H_2O$, 209 ml, 0.318 mol) and added dropwise to the cooled acid solution. After addition was complete the cooling bath was removed and the mixture stirred for 1 h. After this time, MeI (45 mL, 0.725 mol) was added slowly and the mixture stirred overnight at RT. The reaction mixture was diluted with $H_2O$ and transferred to a sep. funnel, the organic was collected and the aqueous portion washed with $Et_2O$ (3×200 mL). The combined organic portion was then washed with 10% citric acid (400 mL) and brine then dried over $Na_2SO_4$, filtered and concentrated at low temp to give a yellow liquid Intermediate C3 (39 g, 88%) which was used without further purification.

To the methyl ester, Intermediate C3 (20 g, 0.131 mol) in toluene (600 mL) cooled to −10° C. was added dropwise Dibal-H (1M in Hex, 0.393 mol, 393 mL). After addition was complete the cooling bath was removed and stirring continued at RT for 2 h, after which the mixture was cooled to 0° C. and MeOH (100 mL) added slowly and carefully to minimize any frothing. Upon addition of MeOH the solution begins to form a gel and becomes difficult to stir with a stirbar. After MeOH addition was complete saturated Rochelle's salt solution (300 mL) was added. At this time the gel began to dissolve. This mixture was stirred for a further 2 h or until the gel completely dissolves and two layers are observed. The mixture was then transferred to a sep. funnel and the organic layer collected. The aqueous layer was washed with EtOAc (3×250 mL). The combined organic portion was washed with brine and dried over $Na_2SO_4$, filtered and concentrated at low temp. to give the product Intermediate C4, as a colorless liquid (15.5 g, 95%).

To a flask charged with alcohol Intermediate C4 (16.7 g, 0.134 mol) and EtOAc (600 mL) was added imidazole (0.469 mol, 32 g). in one portion and the mixture stirred at RT until the imidazole dissolved, once the imidazole dissolved TIPS-Cl (0.201 mol, 43 mL) was added in one portion, a suspension immediately formed, this mixture was stirred overnight at RT. The mixture was filtered and concentrated. The concentrate was suspended in hexane and purified by filtering through $SiO_2$ (300 g) and washing with hexane. The filtrate was concentrated to give the product Intermediate C5 as a colorless liquid (34 g, 90%).

Preparation of Disamylborane $(Sia)_2BH$: To prepare 600 ml of 0.5M $(Sia)_2BH$. To an oven dried three neck round bottom flask equipped with an addition funnel, thermocouple and $N_2$ inlet was added $BH_3$-THF (1M in THF, 0.3 mol, 300 mL) and cooled to 0° C. To this solution was added 2-methyl-2-butene (64 ml, 06 mol) in THF (anh., 236 mL) slowly. The mixture was stirred for 2 h at 0° C. This solution can be stored overnight in the cold room or 2 days in the −40° C. freezer.

An oven dried three neck flask equipped with an addition funnel, thermocouple and $N_2$ inlet, was charged with the TIPS protected di-alkene Intermediate C5 (50 g, 0.178 mol) in THF (anh., 535 mL) and cooled to 0° C. $(Sia)_2BH$ was slowly added via the addition funnel, making sure to not let temperature go over 5° C. After addition was complete the mixture was stirred for a further 2 h at 0° C. At this time NaOH (3N, 148 mL) was added very slowly and carefully to maintain temperature below 10° C. and to minimize frothing. NaOH addition was followed by the addition of $H_2O_2$ (35% in $H_2O$, 47 mL). NB: There is a huge latent exotherm during this addition so the material was added with caution and maintained at a temperature below 10° C. Once addition was complete the cooling bath was removed and the mixture stirred a further 1 h. The mixture was diluted with $H_2O$ and transferred to a sep. funnel the organic was separated and the aqueous was washed with EtOAc (3×300 mL). The combined organic portion was dried over $Na_2SO_4$, filtered and concentrated. The crude material was purified by chromatography on $SiO_2$ (750 g) eluting with 9:1 hexane:EtOAc (6000 mL) followed by 8:2 hexane:EtOAc (2000 mL) to give the product Intermediate C6 as a colorless liquid (39 g, 73%).

A solution containing the TIPS protected olefin Intermediate C6 (8.5 g, 0.028 mol) and THF (anh., 160 mL) was cooled to 0° C. and under a stream of $N_2$ was added $PPh_3$ (0.085 mol, 22.3 g) in one portion. The mixture was stirred until all the $PPh_3$ was dissolved, DEAD (0.085 mol, 13.4 mL) was added drop-wise via addition funnel. After addition was complete the mixture was stirred for 15 min then cyanohydrin (0.085 mol, 7.8 mL) was added slowly. After addition was complete the cooling bath was removed and the mixture was stirred at RT overnight. The reaction mixture was concentrated and the residue taken up in hexane and filtered. The filtrate was concentrated and purified by column chromatography on $SiO_2$ (150 g) eluting with 95:5 hexane:EtOAc to give the product Intermediate C7 as a pale yellow liquid (8.3 g, 95%)

To a solution containing the TIPS protected nitrile Intermediate C7 (12.0 g, 0.039 mol) and THF (60 mL) at room temperature, and under a stream of $N_2$ was added TBAF (59 mL, 0.059 mol, 1M in THF). The reaction mixture was stirred for 3 hr, then diluted with $H_2O$ (250 mL) and transferred to a separatory funnel. The organic layer was separated and the aqueous was extracted with EtOAc (3×100 mL). The combined organic portion was dried over $Na_2SO_4$, filtered and concentrated. The crude product was purified by column chromatography on $SiO_2$ (150 g) eluting with 7:3 hexane:EtOAc to give the product Intermediate C8 as a colorless oil (5.5 g, 93%).

A solution of hydroxynitrile Intermediate C8 (6.0 g, 0.040 mol), $PPh_3$ (15.6 g, 0.060 mol), phthalimide (9.4 g, 0.064 mol) and anh. THF (300 mL) under a stream of $N_2$ at room temperature was added DEAD (10.1 ml, 0.064 mol) over 30 min. After the addition was complete the mixture was stirred for a further 2 hr. after which $H_2O$ (200 mL) was added and the mixture transferred to a sep. funnel. The organic layer was separated and the aqueous layer was extracted with $CH_2Cl_2$ (2×200 mL). The combined organic was dried over $Na_2SO_4$, filtered and adsorbed on $SiO_2$ (50 g). Purification was by column chromatography on $SiO_2$ (200 g) eluting first with 9:1 hexane:EtOAc then with 6:4 hexane:EtOAc to give the product Intermediate C9 as a white solid (11.0 g, 95%).

A solution containing the phthalimide protected nitrile Intermediate C9 (5.0 g, 0.017 mol), hydrazine hydrate (3.4 mL, 0.070 mol) and EtOH (150 mL) was stirred at room temperature for 16 hr. after which conc. HCl (5 mL) was added and the mixture heated at reflux for 1 hr. The mixture was cooled in an ice bath then filtered and the residue washed with ice-cold EtOH. The filtrate was concentrated and again filtered and the residue washed with ice-cold EtOH. The filtrate was again concentrated then triturated with $Et_2O$ to give the product Intermediate C10 as an off-white solid (3.2 g, 98%).

A solution containing the amine salt Intermediate C10 (11.0 g, 0.060 mol), N,N-dimethylurea (5.2 g, 0.060 mol), triethylamine (12.3 mL, 0.090 mol) and EtOH (100 mL) was heated at gentle reflux overnight. The solution was then evaporated and the residue diluted with EtOAc (200 mL) and then washed with $H_2O$ (3×50 mL). The organic portion was dried over $Na_2SO_4$, filtered and concentrated. The crude product was purified by column chromatography on $SiO_2$ (250 g) eluting with 8:3 $Et_2O$:acetone to give the product Intermediate Cl as a colorless substance (8.6 g, 55%).

To a three neck flask equipped with two addition funnels and a nitrogen inlet was added tBuOK (20 mL, 1M in THF, 0.020 mol) at room temperature. To the base was added a solution containing DME (70 mL), the nitrile Intermediate C11 (5.0 g, 0.020 mol) and $TMSCH_2NC$ (2.7 mL, 0.020 mol) slowly. After the addition was complete the mixture was stirred for 45 min. tBuOK (20 mL) was added in one portion followed by the dropwise addition of $TMSCH_2NC$ (2.7 mL) then stirred for 30 min. tBuOK (5 mL) was again, added followed by the dropwise addition of $TMSCH_2NC$ (1.5 mL) then stirred for 30 min. The mixture was stirred for a further 2 hr. The reaction mixture was diluted with $H_2O$ (100 mL) then transferred to a sep. funnel and the organic separated. The aqueous was washed with $CH_2Cl_2$ (3×100 mL). The combined organic was washed with brine, dried over $Na_2SO_4$, filtered and concentrated. The crude material was purified by column chromatography on $SiO_2$ (150 g)

eluting with 16:1 CH$_2$Cl$_2$:MeOH to give the product Intermediate C12 as a colorless liquid (2.6 g, 45%)

To a round bottom flask equipped with an addition funnel and a nitrogen inlet was added NaHCO$_3$ (7.0 g, 0.080 mol) and H$_2$O (25 mL). To this mixture was added the imidazole Intermediate C12 (2.0 g, 0.007) and Et$_2$O (50 mL). The mixture was stirred for 20 min at room temperature. Then a solution containing phenylchlorothionoformate (2.5 mL, 0.018 mol) and Et$_2$O (10 mL) was added slowly. After the addition was complete the mixture was stirred for 4 hr at room temperature then diluted with H$_2$O (100 mL) and transferred to a separatory funnel and the organic separated. The aqueous was washed with Et$_2$O (3×150 mL). The combined organic was washed with brine, dried over Na$_2$SO$_4$, filtered and concentrated. The crude material was diluted with MeOH (40 mL) and Et$_3$N (3.0 mL) added and the mixture stirred at room temperature overnight. To the reaction mixture was added SiO$_2$ (20 g) and the mixture concentrated to dryness. The product was obtained by chromatography on SiO$_2$ (150 g) eluting first with 100% CH$_2$Cl$_2$ (250 mL) followed by 16:1 CH$_2$Cl$_2$:MeOH to give the product Intermediate C13 as a yellow gum (1.0 g, 43%).

In a round bottom flask charged with the imidazole-2-thione Intermediate C13 (0.4 g, 1.2 mmol) dissolved in MeOH (10 mL) was added conc. HCl (0.13 mL, 1.5 mmol) and the mixture stirred for 1.5 hr at room temperature. To the mixture was then added H$_2$O (5 mL) and NaHCO$_3$ (2.5 g, 28 mmol) and stirred for a further 30 min. To this mixture was added SiO$_2$ (20 g) and the solvent evapourated to dryness. The product was obtained by chromatography on SiO$_2$ (50 g), first washing with 100% CH$_2$Cl$_2$ (150 mL) followed by 16:1 CH$_2$Cl$_2$:MeOH, then 100% MeOH. The product was obtained as a yellow solid, which was trituated with ether to give a yellow solid 4-(3-aminomethyl-cyclohex-3-enylmethyl)-1,3-dihydro-imidazole-2-thione Compound 4 (200 mg, 74%).

$^1$H NMR (300 MHz, CD$_3$OD) δ 6.61 (s, 1H), 5.84 (brs, 1H), 3.42 (s, 2H), 2.51-2.47 (m, 2H), 2.17-1.79 (series of m, 5H), 1.20-1.25 (m, 2H).

EXAMPLE B-2

Method B-2

Procedure for the preparation of (+)-(R)-4-(3-Hydroxymethyl-cyclohex-3-enylmethyl)-13-dihydro-imidazole-2-thione (Compound 5)

Compound 5

Compound 5

(+)-(R)

Compound 6

(-)-(S)

Chiral HPLC of Compound 1 under the following conditions: Chiralpak AD® column, 25% EtOH:hexane, rt, uv 280 nm, 1 mL/m, produced the following enantiomers: first eluting (−)-(S)-4-(3-hydroxymethyl-cyclohex-3-enylmethyl)-1,3-dihydro-imidazole-2-thione (Compound 6) (98% ee) and second eluting (+)-(R)-4-(3-hydroxymethyl-cyclohex-3-enylmethyl)-1,3-dihydro-imidazole-2-thione (Compound 5) (97% ee). $^1$H NMR (300 MHz, MeOD-d$^4$) δ 6.57 (s, 1H), 5.64 (brs, 1H), 3.88 (s, 2H), 3.30 (t, J=1.5 Hz, 1H), 2.45 (d, J=6.9 Hz, 2H), 2.10-2.04 (m, 3H), 1.94-1.70 (series of m, 3H), 1.28-1.15 (m, 1H).

EXAMPLE B-3

Method B-3

Procedure for the preparation of (+)-Benzoic acid 5-(2-thioxo-2,3-dihydro-1H-imidazol-4-ylmethyl)-cyclohex-1-enylmethyl ester (Compound 7)

A mixture of (+)-4-(3-hydroxymethyl-cyclohex-3-enylmethyl)-1,3-dihydro-imidazol-2-one (Compound 5) (200 mg, 0.9 mmol) in DMF (1.6 mL) and CH$_2$Cl$_2$ (5 mL) was treated with EDCI (256 mg, 1.34 mmol) benzoic acid (144 mg, 1.18 mmol) and DMAP (32 mg, 0.26 mmol): The mixture was stirred for 24 h at rt. The reaction mixture was diluted with EtOAc (30 mL) and washed with water (1×20 mL), 5% HCl (2×20 mL), brine (1×20 mL). The organic layer was separated and dried over MgSO$_4$. The material was freed of solvent and purified by chromatography on SiO$_2$ with 30% to 50% to 70% EtOAc:hexane to give (+)-benzoic acid 5-(2-thioxo-2,3-dihydro-1H-imidazol-4-ylmethyl)-cyclohex-1-enylmethyl ester (Compound 7) as a foamy solid, 155 mg (53%).

opt. rotation $[\alpha]_D^{20}$+56.3° (c=0.4 in CHCl$_3$)

$^1$H NMR (300 MHz, CDCl$_3$) δ 11.0 (s, 1H), 10.4 (s, 1H), 8.05-8.02 (m, 2H), 7.58-7.42 (m, 3H), 6.43 (s, 1H), 5.81 (s, 1H), 4.66 (s, 2H), 2.56-2.40 (m, 2H), 2.18-1.74 (m, 5H), 1.31-1.24 (m, 2H).

EXAMPLE B-4

Use of cyclopentyl acetic acid (commercially available from Aldrich) in Method B-3 produced (+)-cyclopentyl-acetic acid 5-(2-thioxo-2,3-dihydro-1H-imidazol-4-ylmethyl)-cyclohex-1-enylmethyl ester (Compound 8) (38%).

opt. rotation $[\alpha]_D^{20}$+45° (c=0.25 in CHCl$_3$)

$^1$H NMR (300 MHz, CDCl$_3$) δ 11.4 (brs, 1H), 11.2 (brs, 1H), 6.49 (s, 1H), 5.72 (s, 1H), 4.42 (s, 2H), 2.51-2.48 (m, 2H), 2.35 (d, J=7.5 Hz, 2H), 2.25-2.05 (m, 1H), 1.84-1.16 (series of m, 15H).

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×10$^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors.

brimonidine

The results of the RSAT assay with several exemplary compounds of the invention are disclosed in Table 1 above together with the chemical formulas of these exemplary compounds. NA stands for "not active" at concentrations less than 10 micromolar.

TABLE 1

| Compound | Intrinsic activity | | | |
|---|---|---|---|---|
| | $\alpha_1$ | $\alpha_{2A}$ | $\alpha_{2B}$ | $\alpha_{2C}$ |
| Compound 1 | 0.93 | 0.85 | 0.98 | 1.10 |
| Compound 4 | NA | 0.81 | 0.86 | 0.95 |
| Compound 5 | 1.1 | 0.9 | 1.0 | 1.1 |
| (structure) | NA | NA | NA | NA |

Mouse Model of Tactile Hypersensitivity

Mice (5-6; 25-35 g) are injected with sulprostone (300 ng/kg intraperitoneal), a prostaglandin receptor agonist that activates EP1 prostaglandin receptors. This chemical stimulus results in sensitivity to light stroking of their flanks with a paintbrush, which is assessed every five minutes from 15 minutes to 50 minutes post-injection. Animals are scored as 0 (no response), 1 (avoidance) or 2 (vigorous avoidance, vocalization) every five minutes and the scores are summed to yield a total hypersensitivity score (maximum=16). Sulprostone typically elicits a score of 12-14 and vehicle-treated mice typically exhibit a score of 4-6. Chemical sympathectomy by intraperitoneal injection of 50 mg/kg guanethidine, which causes a depletion of noradrenaline from sympathetic nerve terminals for approximately one week [Malmberg, 1998], markedly reduces the sensitivity of the mice to sulprostone, demonstrating the sympathetic nervous system dependence of this model.

Figure 1:
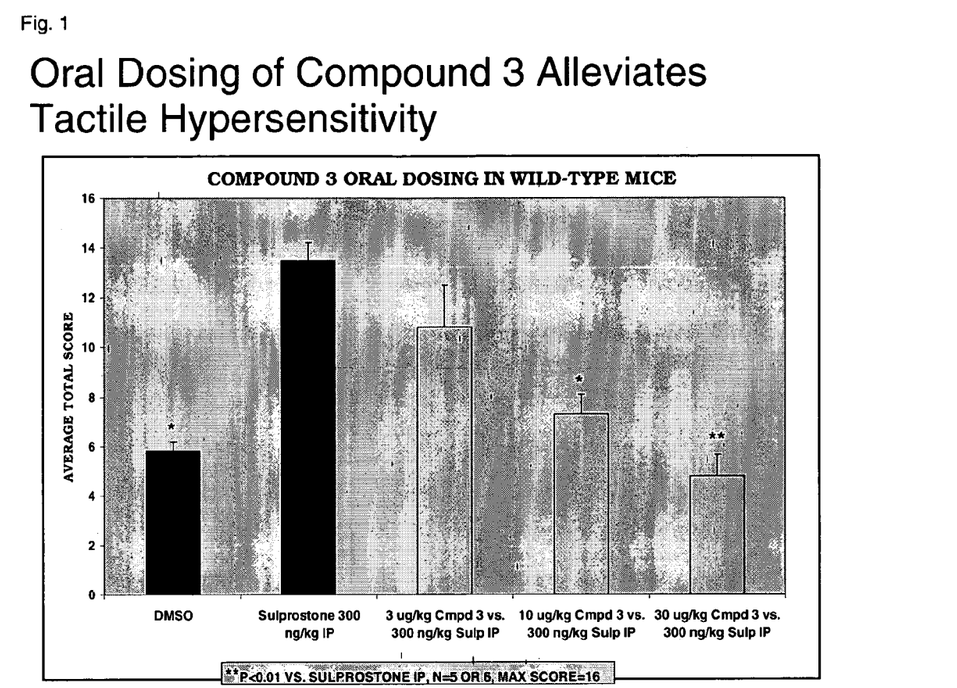
FIG. 1 is a graph showing that oral dosing of compound 3 alleviates tactile hypersensitivity.

Compounds were tested for their ability to reduce the tactile hypersensitivity score when administered 15 min prior to the sulprostone. Compound 1, dosed intraperitoneally, reduced the hypersensitivity in a dose-related manner, with a partial effect at 30 ug/kg and a full effect (score=5) at 100 ug/kg. An oral dose of 300 ug/kg was also active. An ester prodrug, compound 3, was also tested orally. This compound was very potent at alleviating the tactile sensitivity in a dose-related manner (FIG. 1). A full effect was seen at an oral dose of 30 ug/kg.

IOP Model

Male New Zealand Rabbits (6-7; 2-3.5 kg) are used to evaluate drug effects on normotensive IOP measurements. The rabbits are carefully handled so as to minimize excitement. Approximately 25 ul of dilute OphtheticR (0.05%) topical anesthesia is administered to each eye. An initial IOP determination is made in both eyes. Rabbits with 3 mmHg or greater difference in IOP between its right and left eyes are replaced at this time.

Figure 2:
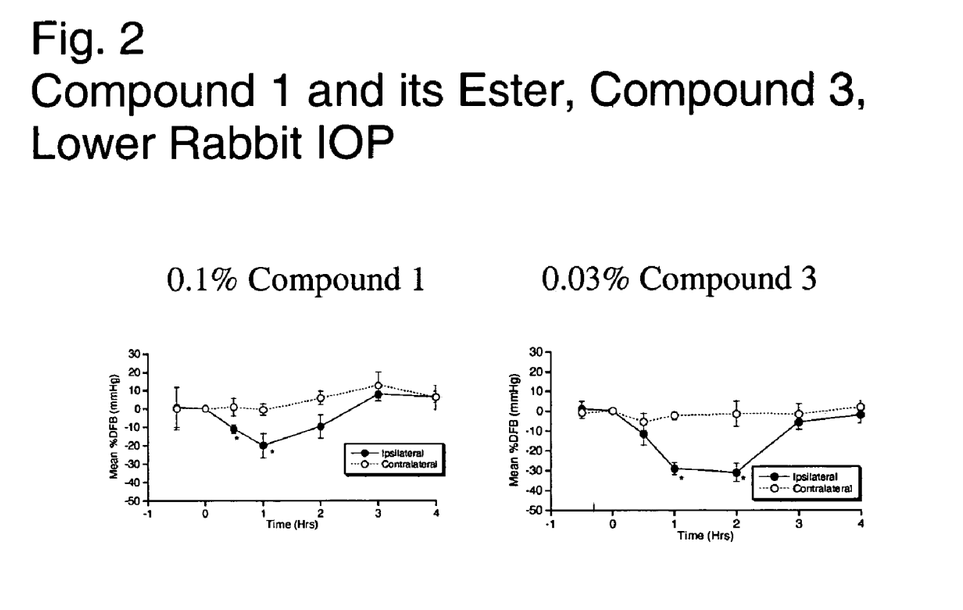
FIG. 2 is two plot which show that compound 1 and its ester, compound 3, lower rabbit IOP.

Immediately following the T=0 reading in both eyes the rabbits are treated with the compound by a topical route. 35 ul of the test solution is instilled onto the cornea of the randomly selected test eye. Pressure readings are taken at various times post-instillation. Animals are kept in their cages with access to food and water between measurements. Pressure readings utilize a Model 30 ClassicTM Pneumatonometer to measure intraocular pressure (IOP) non-invasively through applanation tonometry. compound 1 (0.1%) caused a 20% decrease in IOP and its ester, AGN 204216 (0.03%), caused a 30% decrease in IOP (FIG. 2)

Sedation Model

Figure 3:
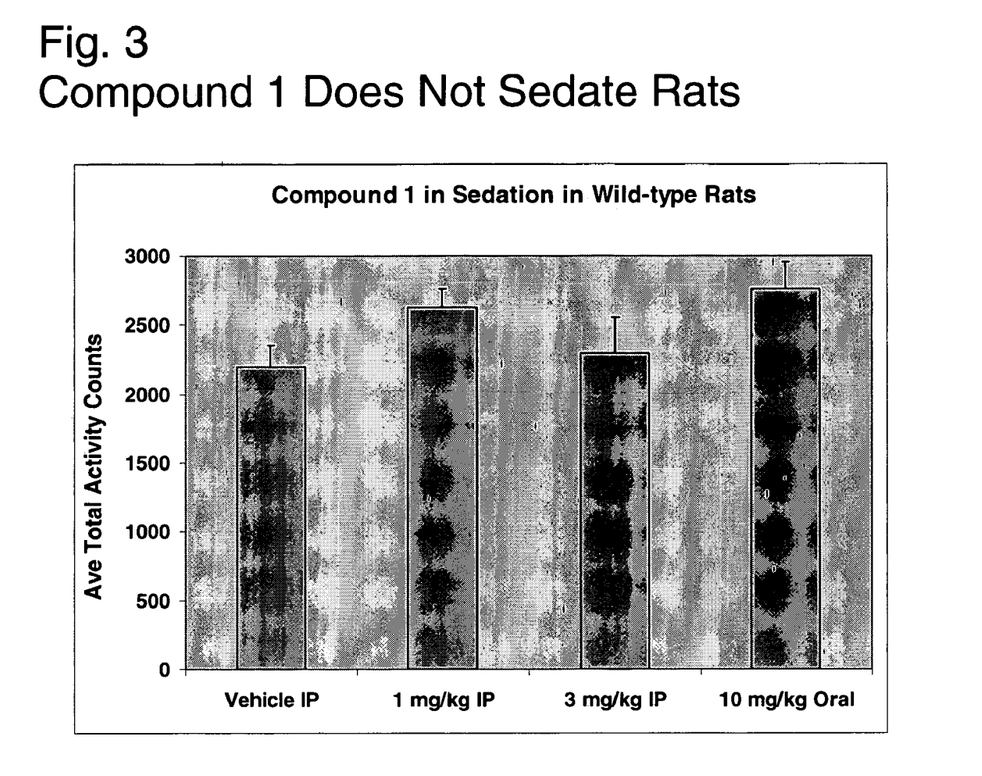
FIG. 3 is a graph showing that compound 1 does not sedate rats.
Figure 4:
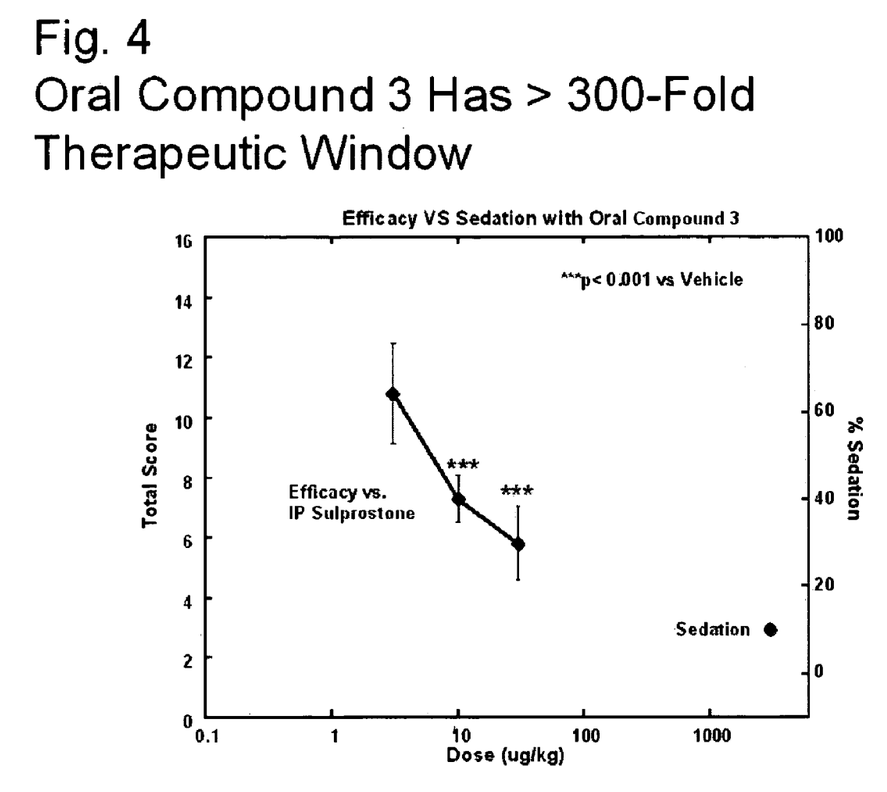
FIG. 4 is a plot showing that oral compound 3 has a therapeutic window >300 fold.

The utility of alpha2-adrenergic agonists is limited by a range of side effects, particularly sedation and cardiovascular depression. The sedative activity of the compounds is assessed by measuring their ability to reduce the exploratory activity of mice and rats when placed in a dark chamber 30 min following dosing. The animal's activity is determined automatically by placing it in a digicom analyzer chamber (Omnitech Electronic). These chambers have photocells criss-crossing the box that are broken as the animal moves around. The computer analyzes this movement and records total activity over a 5-min time period. Alpha2-adrenergic agonists typically inhibit locomotor activity>50% at doses 1 to 10-fold higher than the doses at which they have beneficial effects. The compounds of this invention, however, do not decrease locomotor activity. At intraperitoneal doses up to at least 3 mg/kg and oral doses up to at least 10 mg/kg, compound 1 did not decrease rat locomotor activity (FIG. 3), representing at least a 30-fold margin of safety. The ester, compound 3 did not sedate mice or rats at an oral dose of 3 mg/kg. This represents greater than a 300-fold margin of safety (FIG. 4).

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result Thus, however detailed the foregoing may appear in text, it should not be construed as limiting the overall scope hereof; rather, the ambit of the present invention is to be governed only by the lawful construction of the appended claims.

What is claimed is:

1. A compound of the formula:

or a pharmaceutically acceptable salt or a prodrug thereof; wherein R is OH or $NH_2$.

2. The compound of claim 1 consisting of or a pharmaceutically acceptable salt or a prodrug thereof.

3. The compound of claim 1 consisting of or a pharmaceutically acceptable salt or a prodrug thereof.

4. The compound of claim 1 consisting of 4-(3-Hydroxymethyl-cyclohex-3-enylmethyl)-1,3-dihydro-imidzole-2-thione or a pharmaceutically acceptable salt or a prodrug thereof.

5. The compound of claim 1 consisting of 4-(3-Aminomethyl-cyclohex-3-enylmethyl)-1,3-dihydro-imidazole-2-thione or a pharmaceutically acceptable salt or a prodrug thereof.

6. The compound of claim 1 consisting of 4-(3-Hydroxymethyl-cyclohex-3-enylmethyl)-1,3-dihydro-imidazole-2-thione.

7. A method of reducing intraocular pressure comprising administering a compound according to claim 1 to a mammal in need thereof.

8. A method of treating pain comprising administering a compound according to claim 1 to a mammal in need thereof.

* * * * *